United States Patent [19]
Surayama et al.

[11] Patent Number: 6,051,673
[45] Date of Patent: Apr. 18, 2000

[54] PLATINUM COMPLEX CATALYST COMPOSITION, PROCESS FOR THE PREPARATION THEREOF, AND MICROPARTICULATE THERMOPLASTIC RESIN CATALYST COMPOSITION

[75] Inventors: Toshio Surayama, Midland, Mich.; Masahiko Suzuki, Ichihara, Japan

[73] Assignee: Dow Corning Toray Silicone Co., Ltd., Tokyo, Japan

[21] Appl. No.: 09/121,888

[22] Filed: Jul. 24, 1998

[30] Foreign Application Priority Data

Jul. 28, 1997 [JP] Japan .................................. 9-217193

[51] Int. Cl.$^7$ .................................................. C08G 77/08
[52] U.S. Cl. ............................. 528/15; 502/158; 556/479
[58] Field of Search .............................. 528/15; 502/158; 556/479

[56] References Cited

U.S. PATENT DOCUMENTS

| | | | |
|---|---|---|---|
| 3,419,593 | 12/1968 | Willing | 260/448.2 |
| 3,775,452 | 11/1973 | Karstedt | 260/429 |
| 3,814,730 | 6/1974 | Karstedt | 260/46.5 |
| 4,288,345 | 9/1981 | Ashby | 252/431 |
| 5,994,570 | 11/1999 | Ogawa et al. | 556/11 |
| 5,998,561 | 12/1999 | Jada | 528/15 |

*Primary Examiner*—Robert Dawson
*Assistant Examiner*—Jeffrey B. Robertson
*Attorney, Agent, or Firm*—Richard I. Gearhart; Catherine U. Brown

[57] ABSTRACT

To provide a high-purity platinum complex catalyst composition that has an excellent storage stability, is easy to handle, and has a high catalytic activity. Also, to provide a process for the preparation of this platinum complex catalyst composition and provide a microparticulate thermoplastic resin catalyst composition.

5 Claims, No Drawings

6,051,673

PLATINUM COMPLEX CATALYST COMPOSITION, PROCESS FOR THE PREPARATION THEREOF, AND MICROPARTICULATE THERMOPLASTIC RESIN CATALYST COMPOSITION

FIELD OF THE INVENTION

This invention relates to a platinum complex catalyst composition, a process for the preparation thereof, and a microparticulate thermoplastic resin catalyst composition. More particularly, the present invention relates to a platinum complex catalyst composition that is useful as a catalyst of the hydrosilylation reaction, and also to a process for preparing this composition and to a microparticulate thermoplastic resin catalyst composition.

BACKGROUND OF THE INVENTION

A large number of platinum catalyst compositions are already known for application as catalysts of the hydrosilylation reaction. Among the known platinum catalyst compositions, the platinum-alkenylsiloxane complex catalyst compositions afforded by the reaction of alkenyl-functional siloxane and a platinum compound, e.g., chloroplatinic acid, have particularly high catalytic activities and are useful as catalysts of the hydrosilylation reaction (refer to Japanese Patent Publication (Kokoku) Number Sho 42-22924 (22,924/1967)). However, large amounts of chlorine-containing impurities remain in the platinum complex catalyst compositions afforded by this preparative approach—even when a post-reaction neutralization treatment is carried out. These chlorine-containing impurities cause various problems, such as poisoning of the catalytic reaction and corrosion of surrounding equipment and materials.

Methods directed to ameliorating these problems have also already been proposed. For example, Japanese Patent Publication (Kokoku) Numbers Sho 46-28795 (28,795/1971) and Sho 55-423 (423/1980) teach platinum-alkenylsiloxane complex catalyst compositions that have a reduced content of residual chlorine-containing impurities. These compositions are obtained by causing a neutralizing agent to be present in the reaction between the alkenyl-functional siloxane and chloroplatinic acid. The platinum-alkenylsiloxane complex catalyst compositions afforded by these procedures do provide an inhibition of corrosion of the surroundings and also provide some degree of improvement in the catalytic activity. Unfortunately, the alcohol compound that is present in these platinum-alkenylsiloxane complex catalyst compositions causes undesirable secondary reactions. In particular, the use of these compositions as catalysts of the hydrosilylation reaction is accompanied by the occurrence of such problems as the production of alkoxy groups by a dehydrogenation reaction, a reduction in catalytic activity, and a reduction in storage stability.

Methods that both solve the problems associated with chlorinated impurities and prevent the secondary reactions due to the above-mentioned alcohol compounds have also been examined. In this vein, for example, Japanese Patent Publication (Kokoku) Numbers Sho 46-28795 and Sho 55-423 also teach methods for the high-purity preparation of platinum-alkenylsiloxane complexes by evaporating off the solvent from the platinum-alkenylsiloxane complex catalyst composition. In a departure from other heretofore known methods, Japanese Patent Publication (Kokoku) Number Hei 2-53102 (53,102/1990) teaches a method for the very high-purity preparation of a platinum complex with the same structure. This method involves first mixing a Pt(0)-bis (cyclooctadiene) complex with vinyldisiloxane and subsequently evaporatively eliminating the cyclooctadiene. The platinum catalyst compositions afforded by these methods are highly active and also provide suppression of the reactions secondary to hydrosilylation that are caused by the presence of impurities in the catalyst composition. However, the isolation of these high-purity platinum complexes necessitates a step in which the volatile components are completely removed, and this step itself requires the high-yield recovery of small amounts of a high-viscosity material. In addition, the commercial execution of these methods is highly problematic from an economic point of view. In general, the application of a platinum complex catalyst composition as a hydrosilylation catalyst requires dilution of the composition with solvent or reaction medium prior to its addition to the reaction system, but the high-purity platinum complex catalyst compositions under consideration become unstable when brought into solution, resulting in problems such as rapid decomposition even at room temperature with the production of platinum black and a decline in catalytic activity.

Japanese Patent Publication (Kokoku) Number Hei 3-36573 (36,573/1991) also teaches a method for the preparation of a highly catalytically active platinum catalyst composition for use as a hydrosilylation catalyst. This method, which uses chloroplatinic acid and divinyltetraorganodisiloxane as starting reagents, involves a lengthy reaction under heating until the divinyltetraorganodisiloxane in the system has disappeared due to reaction. The platinum catalyst composition afforded by this method has a high catalytic activity and is easy to handle due to the relatively low viscosities involved. However, the appearance of this platinum catalyst composition ranges from dark brown to black, and it causes product discoloration even when added to the reaction system in just the small amounts required for a catalyst. In addition, platinum black is produced during storage, which results in changes in the catalytic activity during storage.

The present inventors achieved the present invention as a result of extensive investigations directed to solving the problems described above. In specific terms, the object of the present invention is to provide a high-purity platinum complex catalyst composition that is very stable to storage and has a high catalytic activity, a process for the preparation of this composition, and a microparticulate thermoplastic resin catalyst composition.

SUMMARY OF THE INVENTION

The present invention relates to a platinum complex catalyst composition that characteristically comprises
(A) platinum-divinyltetraorganodisiloxane complex,
(B) divinyltetraorganodisiloxane, in an amount such that the number of moles of component (B) is from 2-times to 1,000-times the number of moles of platinum atom in component (A), and
(C) toluene or xylene
wherein the composition contains no more than 5 weight % alcohol compounds and the amount of chlorine atom in the composition does not exceed 0.1-times the number of moles of platinum atoms in component (A). The invention also relates to a process for preparing the subject platinum complex catalyst composition and to a microparticulate thermoplastic resin catalyst composition.

DETAILED DESCRIPTION OF THE INVENTION

To explain the preceding in greater detail, the platinum-divinyltetraorganodisiloxane complex (A) used in the platinum complex catalyst composition according to the present invention is the base ingredient of the composition according to the present invention. This platinum-divinyltetraorganodisiloxane complex is already known and can be readily synthesized, for example, by the reaction of chloroplatinic acid and divinyltetraorganodisiloxane with heating (refer to Japanese. Patent Publication (Kokoku) Numbers Sho 42-22924, Sho 46-28795, and Sho 55-423 and Japanese Patent Publication (Kokoku) Number Hei 2-53102).

The divinyltetraorganodisiloxane (B) used in the platinum complex catalyst composition according to the present invention can be exemplified by compounds with the following general formula $$CH_2=CH(R^1)(R^2)Si—O—Si(R^1)(R^2)CH=CH_2$$

in which $R^1$ and $R^2$ are selected from alkyl groups such as methyl and ethyl, alkenyl groups such as vinyl and allyl, aryl groups such as phenyl, and perfluoroalkyl groups. Component (B) can be specifically exemplified by compounds with the following chemical structures.

$$CH_2=CH(CH_3)_2Si—O—Si(CH_3)_2CH=CH_2$$

$$CH_2=CH(CH_3)(C_6H_5)Si—O—Si(CH_3)(C_6H_5)CH=CH_2$$

$$CH_2=CH(C_6H_5)_2Si—O—Si(C_6H_5)_2CH=CH_2$$

$$(CH_2=CH)_2(CH_3)Si—O—Si(CH_3)(CH=CH_2)_2$$

Among the preceding, the compound with the formula $$CH_2=CH(CH_3)_2Si—O—Si(CH_3)_2CH=CH_2$$

is recommended because it is easy to acquire and is associated with little secondary reaction during reaction. Component (B) is added in an amount such that the number of moles of component (B) is from 2-times to 1,000-times, preferably from 3-times to 500-times, and more preferably from 3-times to 20-times the number of moles of platinum atoms originating from component (A) in the invention composition.

Component (C), which is a solvent added for the purpose of dilution, is selected from toluene and xylene. Combinations of toluene and xylene may also be used. While the addition of component (C) can be freely selected, at a practical level it is preferably added in an amount that brings the platinum metal content in the invention composition to 0.1 to 10 weight %.

The platinum complex catalyst composition according to the present invention comprises the components (A) to (C) described above, but in addition this composition must not contain more than 5 weight % alcohol compounds. In a preferred embodiment alcohol compounds are essentially not present. When more than 5 weight % alcohol compound is present, secondary reactions will occur when the invention composition is used as a catalyst of the hydrosilylation reaction. For the present purposes the amount of alcohol compound is the amount as measured by gas chromatography. The amount as measured by gas chromatography is preferably 0. In addition, the number of moles of chlorine atoms in the subject composition must not exceed 0.1-times the number of moles of platinum atoms in component (A). In a preferred embodiment the chlorine atom is essentially not present. When the amount of chlorine atom, expressed in terms of number of moles, exceeds 0.1-times the number of moles of platinum atoms in component (A), the invention composition will suffer from a drastically reduced storage stability and, depending on the particular circumstances, problems will appear in reaction systems to which the composition has been added as catalyst, e.g., the occurrence of secondary reactions and catalyst deactivation. The amount of chlorine atom can be measured for the present purposes by, for example, silver nitrate titration.

The platinum complex catalyst composition according to the present invention is preferably prepared by first reacting chloroplatinic acid or metal salt thereof, divinyltetraorganodisiloxane, and a basic inorganic metal salt in an alcohol solvent with the formula $C_nH_{2n-1}OH$ (where n in the formula is an integer from 2 to 4) with heating, subsequently adding toluene or xylene, and then distilling out the alcohol.

This preparative process will be explained in greater detail in the following. Chloroplatinic acid is the compound $H_2PtCl_m$ (where m is 4 or 6), while the metal salt refers to the alkali metal salts of chloroplatinic acid. Chloroplatinic acid is generally a solid containing water of crystallization, but it may also be used as its aqueous solution. However, because the yield declines when too much water is introduced into the reaction system along with the chloroplatinic acid, the platinum concentration in the solid or aqueous solution is preferably at least 20 weight % as the platinum atom. The alkali metal salts of chloroplatinic acid can be exemplified by sodium chloroplatinate and potassium chloroplatinate with sodium chloroplatinate being preferred based on solubility considerations.

The divinyltetraorganodisiloxane is a compound as described above, and the amount of divinyltetraorganodisiloxane added to the reaction must be at least 2-times on a molar-equivalent basis the amount of platinum atom in the chloroplatinic acid or metal salt thereof and preferably is at least 3-times on a molar-equivalent basis the amount of platinum atom in the chloroplatinic acid or metal salt thereof. Addition of the divinyltetraorganodisiloxane in an amount smaller than the specified lower limit results in an increased precipitation of platinum black during the reaction and hence in a drastically reduced yield. The use of excessively large amounts of divinyltetraorganodisiloxane results in an excessively large decline in the platinum content in the target platinum catalyst composition and is also economically undesirable. The reaction is therefore preferably carried out using no more than 20-times on a molar-equivalent basis the amount of platinum in the chloroplatinic acid.

The basic inorganic metal compound is an essential component that functions to neutralize the chloroplatinic acid and to remove from the system the chlorine-containing components (mainly hydrogen chloride) that are produced during the reaction of chloroplatinic acid or metal salt thereof with divinyltetraorganodisiloxane. Specific examples of basic inorganic metal compounds useable in the present invention are metal salts such as sodium carbonate, sodium bicarbonate, and potassium carbonate, and also sodium hydroxide and potassium hydroxide. Sodium carbonate and sodium bicarbonate are recommended based on the neutralization efficiency and the ease of removal from the system after the reaction. The subject basic inorganic metal compound must be employed in a quantity sufficient to neutralize the chlorine in the chloroplatinic acid—absent which noneliminable chlorine-containing impurities will remain in large amounts in the platinum catalyst composition produced by the reaction.

The alcohol compound $C_nH_{2n-1}OH$ (where n is an integer from 2 to 4) is an essential component that functions as a solvent in the reaction for synthesizing the platinum complex catalyst composition according to the present invention, that functions to accelerate this reaction, and that also functions to stabilize the platinum compound that is produced. The subject alcohol compound can be specifically exemplified by ethanol, n-propanol, isopropanol, n-butanol, isobutyl alcohol, and tert-butyl alcohol. The alcohol compound will generally be added at from 20- to 1,000-times on a weight basis the amount of platinum in the chloroplatinic acid or salt thereof. The addition of less alcohol compound runs the risk of such problems as an excessively high reaction system viscosity and a substantial increase in the production of platinum black during the reaction. The addition of more alcohol compound causes an excessively large decline in the reactor utilization efficiency and an excessively large decline in the platinum concentration in the target platinum catalyst composition.

While the synthesis is carried out by reacting chloroplatinic acid or metal salt thereof, divinyltetraorganodisiloxane, and basic inorganic metal compound in an alcohol solvent with heating, other components may be present insofar as they do not exercise a negative influence on the reaction. These other components can be exemplified by organic solvents such as toluene and xylene and by organosiloxane oligomers.

In the first step in a preferred method according to the present invention for preparing the platinum complex catalyst composition, chloroplatinic acid or metal salt thereof, divinyltetraorganodisiloxane, and basic inorganic metal compound are reacted by heating in the alcohol. Heating can be carried out after all four of these compounds have been introduced, or a mixture of the divinyltetraorganodisiloxane, basic inorganic metal compound, and alcohol can first be heated and an aqueous or alcoholic solution of chloroplatinic acid can then be added dropwise. Heating is generally carried out at a temperature in the vicinity of the reflux temperature of the alcohol. This reaction runs relatively rapidly. For example, in the case of chloroplatinic acid ($H_2PtCl_6 \cdot nH_2O$) the reaction is almost complete within 1 hour after reaching the reflux temperature. After the end of the reaction the reaction product can be filtered to remove the basic inorganic metal compound and its neutralization salt.

After the reaction as described above, the preparative method according to the present invention continues with the addition of toluene or xylene and subsequent removal of the alcohol. The alcohol will generally be removed by distillation with heating under reduced pressure. The opportunity to azeotropically distill out the water in the system during alcohol distillation should also be taken into consideration. The sources of water are the solvent used to dissolve the chloroplatinic acid, the water of crystallization in the chloroplatinic acid, and water produced as a secondary product during neutralization by the basic inorganic metal compound. The water and alcohol often cause problems such as the occurrence of secondary reactions during the hydrosilylation reaction and an increase in adhesiveness for the interior walls of the container during preparation of the microparticulate thermoplastic resin catalyst (discussed below). It is for these reasons that the water is preferably distilled from the system along with the alcohol. The toluene or xylene also azeotropically distills out during distillation of the alcohol. When too much of the solvent is volatilized off during this solvent exchange step, the viscosity of the system will become excessively high and solidification may even occur. When these conditions prevail, the temperature distribution in the reactor will become inhomogeneous and problems such as an increase in platinum black production will occur. The toluene or xylene must therefore be added in sufficient amount to avoid these problems. As a general rule, the toluene or xylene should be added in an amount about equal to up to about 5-times the amount of alcohol present in the system post-reaction. When large amounts of alcohol are present, it is recommended that the toluene or xylene be replenished during the course of heating and elimination. The alcohol is preferably completely eliminated.

The platinum complex catalyst composition according to the present invention can be directly used as a catalyst of the hydrosilylation reaction. However, in some cases salts that were dissolved in the system prior to the solvent exchange step may have precipitated, in which case they are preferably removed by, for example, filtration. In addition, in order to improve the ease of use in application as a platinum complex catalyst, in a preferred embodiment the platinum content in the solution is measured and the solution is then diluted with some amount of toluene or xylene in order to supply a catalyst with a constant platinum concentration continuously over time.

The platinum complex catalyst composition according to the present invention as described above is very pure, has a high catalytic activity and an excellent storage stability, is easy to handle, resists discoloration, and contains little impurity. As a consequence, the subject composition will be useful as a hydrosilylation catalyst where these features are critical. The subject composition is in particular useful as a catalyst of the hydrosilylation of carbon-carbon multiple bonds by silicon-bonded hydrogen. For example, during the process of bonding a carbon-carbon multiple bond-functional organic compound into polyorganosiloxane that contains a plural number of SiH in each molecule to prepare a so-called organofunctional polyorganosiloxane, a dehydrogenative alkoxylation occurs as a secondary reaction at the expense of hydrosilylation when alcohol is present in the system and the resulting products cannot be removed from the system. Use of the platinum complex catalyst composition according to the present invention in such cases permits the high-purity synthesis of the target organofunctional polyorganosiloxane without the occurrence of secondary reactions.

The platinum complex catalyst composition according to the present invention comprises the components (A) to (C) as described above, but this platinum complex catalyst composition can also be used to make microparticulate thermoplastic resin catalysts containing a platinum complex catalyst composition through the use of thermoplastic resin and organic solvent with a boiling point below toluene in addition to components (A) to (C). The subject microparticulate thermoplastic resin catalysts containing a platinum complex catalyst composition are already known in the form of microcapsulated catalysts, and methods for their preparation are also known (for example, refer to Japanese Patent Publication (Kokoku) Number Hei 5-58450 (58,450/1993)). The microparticulate thermoplastic resin catalyst composition according to the present invention can be prepared using the platinum complex catalyst composition according to the present invention as follows. A composition is first prepared by the addition of thermoplastic resin and organic solvent with a bp below toluene to the platinum complex catalyst composition comprising components (A) to (C) as described above. The resulting composition is then sprayed into a hot gas and the toluene or xylene and organic solvent boiling below toluene are driven off and removed while the composition is in the atomized state to complete the preparation. Since this method affords a microparticulate thermoplastic resin catalyst composition with an average particle diameter of no more than 10 micrometers, adhesion to the equipment during preparation can be a problem. However, use of the platinum complex catalyst composition according to the present invention results in a substantial weakening and reduction of adhesion to the equipment. Moreover, use of the platinum complex catalyst composition according to the present invention also avoids the equipment corrosion caused by the presence of residual chlorine-containing impurities.

EXAMPLES

The present invention will be explained in greater detail below through working examples. In the examples % denotes weight %, Me represents the methyl group, and Ph represents the phenyl group.

Reference Example 1
Synthesis of a platinum-divinyltetramethyldisiloxane complex catalyst 3.0 kg chloroplatinic acid crystals (40% platinum content) and 15.0 kg isopropanol were placed in a 50-L reactor, and 6.0 kg sodium bicarbonate and 6.0 kg 1,3-divinyltetramethyldisiloxane were then added while stirring. The resulting suspension was heated while stirring. After reacting for 30 minutes at 65 to 75° C., the reaction mass was cooled and the solids were filtered off to give 22.0 kg of an isopropanol solution of platinum-divinyltetramethyldisiloxane complex catalyst. The platinum content was 4.1% as measured by x-ray fluorescence analysis, and the 1,3-divinyltetramethyldisiloxane content as measured by gas chromatography was 9.4%.

Example 1

0.5 kg 1,3-divinyltetramethyldisiloxane, 35 kg toluene, and 1.5 kg sodium bicarbonate were added to 15.0 kg of the isopropanol solution of platinum-divinyltetramethyldisiloxane complex catalyst that was prepared in Reference Example 1. The system was then heated after dropping the pressure to 200 torr. Distillation of the solvent began once the liquid temperature reached 45° C., and heating was ended when the liquid temperature reached 60° C. 32 L of solvent were distilled out during this interval. Filtration of the suspension in the reactor gave 22.6 kg of a toluene solution of platinum-divinyltetramethyldisiloxane complex catalyst. The platinum content as measured by x-ray fluorescence analysis was 2.8%, the 1,3-divinyltetramethyldisiloxane content as measured by gas chromatography was 6.8%, and isopropanol was not detected. The content of the chlorine atom as determined by silver nitrate titration was 0.01%. This toluene solution was diluted with toluene to bring the platinum content to 2.0%, yielding 31.6 kg toluene solution of platinum-divinyltetramethyldisiloxane complex catalyst.

Example 2

100 g siloxane with the following average molecular formula

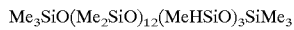
$Me_3SiO(Me_2SiO)_{12}(MeHSiO)_3SiMe_3$ and 560 g polyether with the following average molecular formula

$CH_2=CHCH_2-O-(CH_2CH_2O)_{28}(CH_2CHCH_3O)_{12}CH_3$ were introduced into a stirrer-equipped 1-liter four-neck flask. To this was also added 0.68 g of the toluene solution of platinum-divinyltetramethyldisiloxane complex catalyst that was synthesized in Example 1 (corresponding to 21 ppm as platinum atom referred to the total weight of the siloxane and polyether). After gradually heating, a reaction was run for 2 hours at a liquid temperature of 100° C. and the reaction was then ended by dropping the temperature. Analysis of the reaction product by $^{29}$Si-NMR demonstrated that the MeHSiO unit had entirely disappeared and had been entirely converted into the MeRSiO unit.

Reference Example 2

The platinum-divinyltetramethyldisiloxane complex catalyst prepared in Reference Example 1 was diluted with isopropanol to give an isopropanol solution of platinum-divinyltetramethyldisiloxane complex catalyst with a platinum content of 2.0%.

Comparative Example 1

A reaction was run as in Example 2, but in this case replacing the toluene solution of platinum-divinyltetramethyldisiloxane catalyst synthesized in Example 1 and used in Example 2 with 0.68 g of the isopropanol solution of platinum-divinyltetramethyldisiloxane complex catalyst that was synthesized in Reference Example 2 (corresponding to 21 ppm as platinum atom referred to the total weight of the siloxane and polyether). Analysis of the reaction product by $^{29}$Si-NMR again confirmed that all the MeHSiO unit had disappeared, but in this case it was also found that 4 mole % of the siloxane units that should have been converted to the MeRSiO unit had in fact become the Me(RO)SiO unit (chemical shift –60 ppm using TMS as standard). The presence of this siloxane unit indicated that the starting siloxane had reacted with the isopropanol present in the complex catalyst at the expense of bonding with the polyether through the hydrosilylation reaction.

Example 3

0.26 kg 1,3-divinyltetramethyldisiloxane and 250 kg dichloromethane were added to 86.3 kg of a toluene solution containing 60% thermoplastic silicone resin that had the average unit formula $(PhSiO_{3/2})_{0.78}(Me_2SiO)_{0.22}$ and a glass-transition temperature of 66.5° C. This was followed by the addition with mixing of 10.4 kg of the toluene solution of platinum-divinyltetramethyldisiloxane complex catalyst that was prepared in Example 1. A homogeneous solution of thermoplastic silicone resin and platinum-divinyltetramethyldisiloxane complex catalyst was obtained.

Example 4

Using a dual-fluid nozzle, the homogeneous solution of complex catalyst and thermoplastic silicone resin prepared in Example 3 was continuously sprayed into a spray dryer chamber (Ashizawa Niro Atomizer Co., Limited) that used nitrogen for the hot gas flow. The temperature of the hot nitrogen flow was 80° C. at the inlet to the spray dryer and 45° C. at the outlet to the spray dryer. The velocity of the hot gas flow was 1.3 m³/minute. 415 g silicone resin micropowder containing platinum-divinyltetramethyldisiloxane complex composition was collected by a bag filter during operation for 1 hour. The average particle size of this micropowder was 1.5 μm, and its platinum content was 0.40%. After the halt of operations, the accumulated depth of adhered powder in the conduit of the curved element connecting the spray dryer body and the bag filter was measured at 0.2 mm.

Reference Example 3

A homogeneous solution of complex and thermoplastic silicone resin was prepared as in Example 3, but in this case using 5.1 kg of the isopropanolic complex solution prepared in Reference Example 2 in place of the toluenic complex solution prepared in Example 1 and used in Example 3.

Comparative Example 2

A silicone resin micropowder was prepared as in Example 4, but in this case using the homogeneous solution of thermoplastic silicone resin and isopropanolic complex solution prepared in Reference Example 3 in place of the toluenic complex solution prepared in Example 3 and used in Example 4. In this case collection by the bag filter during operation for 1 hour afforded 350 g silicone resin micropowder containing platinum-divinyltetramethyldisiloxane complex composition. The average particle size of this micropowder was 1.5 μm, and its platinum content was 0.40%. After the halt of operations, the accumulated depth of adhered powder in the conduit of the curved element connecting the spray dryer body and the bag filter was measured at 1.8 mm.

What is claimed:

1. A composition comprising:
   (A) a platinum-divinyltetraorganodisiloxane complex,
   (B) a divinyltetraorganodisiloxane, in an amount such that the number of moles of component (B) is from 2-times to 1,000-times the number of moles of platinum atom in component (A), and
   (C) toluene or xylene
   wherein the composition contains no more than 5 weight % alcohol compounds and the number of moles of chlorine atoms in the composition does not exceed 0.1-times the number of moles of platinum atoms in component (A).

2. The composition of claim 1, in which the content of alcohol compounds as measured by gas chromatography is 0.

3. The composition of claim 1, additionally comprising a thermoplastic resin and an organic solvent with a boiling point below that of toluene.

4. A process for preparing a microparticulate thermoplastic resin catalyst, comprising the steps of:
   1) preparing a platinum-divinyltetraorganodisiloxane complex composition by a method comprising
      i) reacting chloroplatinic acid or metal salt thereof, divinyltetraorganodisiloxane, and a basic inorganic metal salt in an alcohol solvent with the formula $C_nH_{2n-1}OH$ and where n is an integer from 2 to 4;
      ii) heating;
      iii) adding a solvent selected from the group consisting of toluene, xylene, and combinations thereof; and
      iv) distilling out the alcohol solvent;
   2) adding a thermoplastic resin and an organic solvent having a boiling point below toluene to the product of step 1)
   3) spraying the product of step 2) into a hot gas;
   4) removing the solvent selected from the group consisting of toluene, xylene, and combinations thereof, and the organic solvent having a boiling point below toluene.

5. The composition of claim 3, wherein said composition is sprayed into a hot gas and eliminating therefrom the toluene or xylene and organic solvent with a boiling point below that of toluene while the composition is in the atomized state.

* * * * *